United States Patent [19]

Ohno et al.

[11] 4,003,936
[45] Jan. 18, 1977

[54] 2-HYDROCINNAMPYL-1,3-CYCLOPEN-TANEDIONES

[75] Inventors: Masaji Ohno; Mutsuo Kataoka; Norio Kawabe, both of Kamakura, Japan

[73] Assignee: Zaidan Hojin Biseibutsu Kagaku Kenkyu Kai, Tokyo, Japan

[22] Filed: Nov. 26, 1971

[21] Appl. No.: 202,597

[30] Foreign Application Priority Data

Dec. 15, 1970 Japan ............................ 45-111292
Mar. 8, 1971 Japan ............................ 46-11787
Apr. 15, 1971 Japan ............................ 46-23501

[52] U.S. Cl. .......................... 260/590 C; 260/338; 260/340.7; 260/340.9; 260/465 R; 260/465 D; 260/465 E; 260/465 F; 260/465 G; 260/465 H; 260/469; 260/471 R; 260/47 C; 260/473 R; 260/475 P; 260/488 CD; 260/558 A; 260/559 R; 260/568; 260/574; 260/575; 260/577; 260/590 E; 424/278; 424/282; 424/285; 424/300; 424/304; 424/358; 424/309; 424/310; 424/324; 424/330; 424/331

[51] Int. Cl.² .................. C07C 49/76; C07C 49/80; C07C 49/82; C07C 49/84

[58] Field of Search ..................... 260/590, 590 C

[56] References Cited

UNITED STATES PATENTS 3,391,165   7/1968   Hughes et al. .............. 260/590 X
3,644,502   2/1972   Morin et al. ................ 260/590 X

OTHER PUBLICATIONS

Tanaka, "Chem. Ab." vol. 73, p. 14487h (1970).

*Primary Examiner*—Norman Morgenstern
*Attorney, Agent, or Firm*—Brady, O'Boyle & Gates

[57] ABSTRACT

As new compound, a series of 2-hydrocinnamoyl-1,3-cyclopentanedione derivative of the general formula:

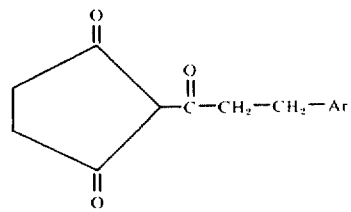

wherein Ar stands for a mono-valent aromatic radical, for example, phenyl and 3,4-methylenedioxy-phenyl, substituted or unsubstituted, have been found to have an activity to inhibit the action of tyrosine hydroxylase and to be useful as hypotensive agent. These new compounds may be produced by condensing 2-acetyl-1,3-cyclopentanedione with an aromatic aldehyde of the formula Ar-CHO wherein Ar is as defined, according to Claisen-Schmidt condensation, followed by the hydrogenation of the condensation product obtained, or the new compounds may also be produced by reacting 2-acetyl-1,3-cyclopentanedione with an aromatic halide of the formula Ar-CH$_2$X wherein Ar is as defined and X is a halogen, for example, in liquid ammonia and in the presence of an alkali metal amide.

13 Claims, No Drawings

2-HYDROCINNAMPYL-1,3-CYCLOPENTANED-IONES

This invention relates to derivatives of 1,3-cyclopentanedione and particularly derivatives of 2-hydrocinnamoyl-1,3-cyclopentanedione as new compounds which are useful as hypotensive agent. Further, this invention relates to processes for the production of these new and useful derivatives of 1,3-cyclopentanedione and particularly of 2-hydrocinnamoyl-1,3-cyclopentanedione.

Many attempts have been made to synthesize new chemical compounds which are useful as medicine. An object of the present invention is to provide new hypotensive agents and to provide simple and efficient processes for the production of such new hypotensive agents.

We have now succeeded in synthesizing new derivatives of 1,3-cyclopentanedione and particularly new derivatives of 2-hydrocinnamoyl-1,3-cyclopentanedione of the general formula:

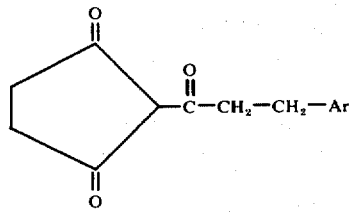

wherein Ar stands for a mono-valent aromatic radical such as phenyl and 3,4-methylenedioxy-phenyl which may be substituted or un-substituted, and we have now found that the new derivatives of 1,3-cyclopentanedione of the above general formula exhibit a remarkable effect as a blood-pressure reducing agent or hypotensive agent because they have useful activity of reducing the blood pressure, low toxicity and high biochemical activity of inhibiting the action of tyrosine hydroxylase and of inhibiting the bio-synthesis of norepinephrine.

According to an aspect of the present invention, thereofre, there is provided a derivative of 1,3-cyclopentanedione of the general formula:

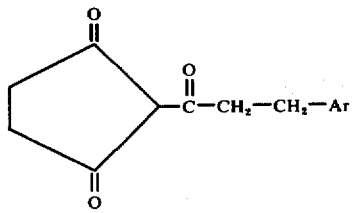

[I]

wherein Ar stands for a mono-valent aromatic radical, substituted or un-substituted.

According to a preferred embodiment of the first aspct of the present invention, there is provided a derivative of 2-hydrocinnnamoyl-1,3-cyclopentanedione of the general formula:

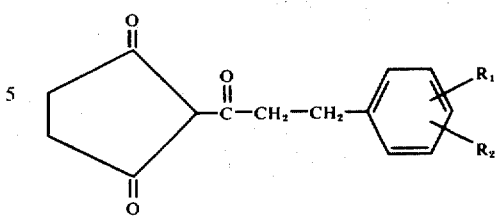

[Ia]

wherein $R_1$ and $R_2$ may be the same or different and are a hydrogen atom, a halogen atom (for example, chlorine, bromine, iodine, fluorine), hydroxyl, nitro, cyano, trifluoromethyl, a lower alkyl of 1–4 carbon atoms, preferably an alkyl of 1–3 carbon atoms (for example, methyl, ethyl, n-propyl and iso-propyl), a lower alkoxyl of 1–4 carbon atoms, preferably an alkoxyl of 1–3 carbon atoms (for example, methoxyl, ethoxyl, n-propoxyl and iso-propoxyl), carbamoyl -$CONH_2$, a substituted amino group -NR'R", an alkoxycarbonyl group -CO-OR' or an acyloxyl group -O-OCR' in which R' and R" are a lower alkyl of 1–4 carbon atoms, preferably an alkyl of 1–3 carbon atoms (for example, methyl, ethyl, n-propyl and iso-propyl); or $R_1$ and $R_2$ together may form an alkylenedioxy chain -O-R'''-O- in which R''' is a lower alkylene of 1–4 carbon atoms, preferably an alkylene of 1—3 carbon atoms (for example, methylene and 1,1-ethylene). The new derivative of 2-hydrocinnamoyl-1,3-cyclopentanedione of the formula [Ia] exhibits particularly higher effects as the hypotensive agent.

According to a more limited form of the first aspect of the present invention, there is provided a derivative of 2-hydrocinnamoyl-1,3-cyclopentanedione of the formula:

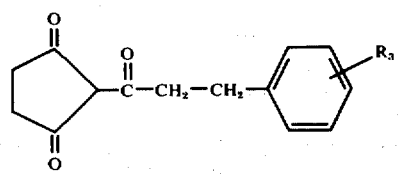

[Ib]

wherein $R_3$ is selected from a hydrogen atom, a halogen atom (for example, chlorine, bromine, iodine and fluorine), hydroxyl, nitro, a lower alkoxyl of 1–4 carbon atoms and a substituted amino group -NR'R" in which R' and R" are a lower alkyl of 1–4 carbon atoms.

According to another limited form of the first aspect of the present invention, there is provided a derivative of 2-hydrocinnamoyl-1,3-cyclopentanedione of the formula:

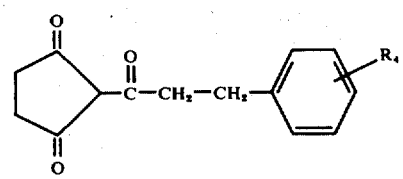

[Ic]

wherein $R_4$ is a hydrogen atom or a lower alkyl of 1–4 carbon atoms, for example, methyl.

According to a further limited form of the first aspect of the present invention, there is provided a derivative of 2-hydrocinnamoyl-1,3-cyclopentanedione of the formula:

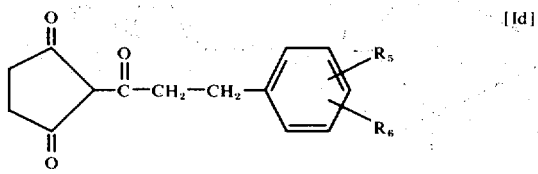

wherein $R_5$ and $R_6$ may be the same or different and are selected from a halogen, hydroxyl, a lower alkyl of 1–4 carbon atoms, a lower alkoxyl of 1–4 carbon atoms, a lower acyloxy of 1–4 carbon atoms, for example, acetoxy and an alkylenedioxy chain -O-R'''-O- in which R''' is a lower alylene of 1–4 carbon atoms such as methylene and 1,1-ethylene.

Among the new compounds of the present invention, the following compounds as specified below are remarkably effective as the hypotensive agent;

1. 2-(Hydrocinammoyl)-1,3-cyclopentanedione.
2. 2-(2-Hydroxyhydrocinnamoyl)-1,3-cyclopentanedione.
3. 2-(3-Hydroxyhydrocinnamoyl)-1,3-cyclopentanedione.
4. 2-(4-Hydroxyhydrocinnamoyl)-1,3-cyclopentanedione.
5. 2-(3,4-Dihydroxyhydrocinnamoyl)-1,3-cyclopentanedione.
6. 2-(4-Chlorohydrocinnamoyl)-1,3-cyclopentanedione.
7. 2-(4-Fluorohydrocinnamoyl)-1,3-cyclopentanedione.
8. 2-(4-Nitrohydrocinnamoyl)-1,3-cyclopentanedione.
9. 2-(4-Methylhydrocinnamoyl)-1,3-cyclopentanedione.
10. 2-(4-Methoxyhydrocinnamoyl)-1,3-cyclopentanedione.
11. 2-(4-Methoxycarbonylhydrocinnamoyl)-1,3-cyclopentanedione.

In the presence of a metal cation $M^{n+}$, the compound of the formula [I] forms a salt of the formula:

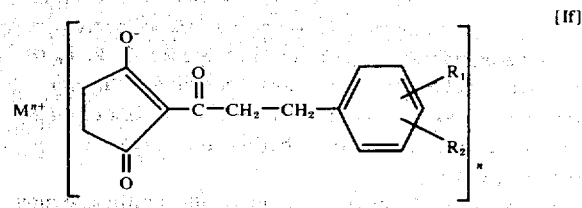

wherein $M^{n+}$ means a pharmaceutically acceptable metal cation of the valency $n$ such as monovalent cation, for example, an alkali metal cation such as sodium cation, and divalent cation, for example, an alkaline earth metal cation such as calcium cation and Ar is as defined in the above. Together with a metal cation $M^{n+}$, the compound of the formula [Ia] forms a salt of the formula:

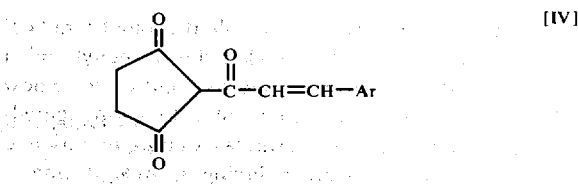

wherein $M^{n+}$ means a pharmaceutically acceptable metal cation of the valency $n$, for example, an alkali metal cation or an alkaline earth metal cation and $R_1$ and $R_2$ are as defined in the above.

The new derivatives of 2-hydrocinnamoyl-1,3-cyclopentanedione of the general formula [I] and particularly of the formula [Ia] may readily be produced by the following two processes.

The first process which may be used comprises two successive steps, a step of subjecting 2-acetyl-1,3-cyclopentanedione [II] and a substituted or un-substituted aromatic aldehyde [III] of the formula:

Ar—CHO     [III]

wherein Ar is as defined in the above to Claisen-Schmidt condensation in a usual manner to give 2-cinnamoyl-1,3-cyclopentanedione or a substituted derivative thereof [IV] of the formula:

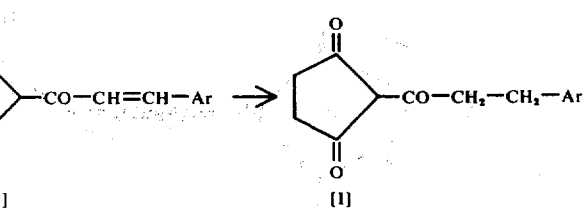

wherein Ar is as defined above, as the condensation product, and a further step of reducing or hydrogenating this condensation product [IV] in a usual manner to give the derivative of 1,3-cyclopentanedione of the formula [I].

The first process may be shown by the following equation.

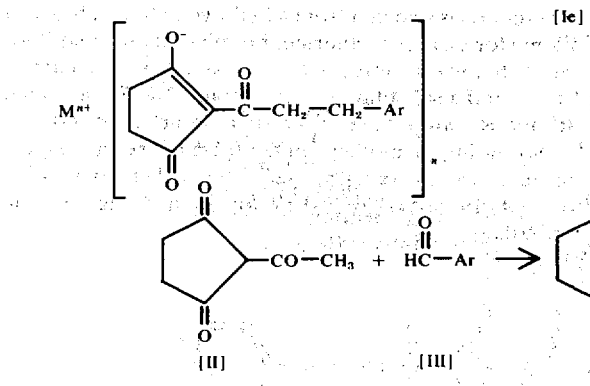

According to a second aspect of the present invention, therefore, there is provided a process for the production of a derivative of 1,3-cyclopentanedione of the general formula:

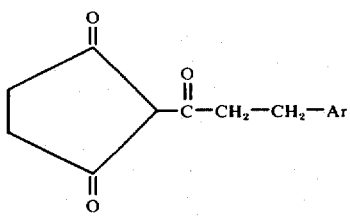

[I]

wherein Ar stands for a mono-valent aromatic radical, substituted or un-substituted, which comprises subjecting 2-acetyl-1,3-cyclopentanedione of the formula:

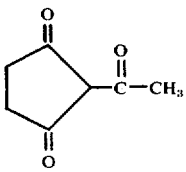

[II]

and an aromatic aldehyde of the formula:

Ar—CHO   [III]

wherein Ar is as defined above to Claisen-Schmidt condensation in a usual manner to give a derivative of 1,3-cyclopentanedione of the formula:

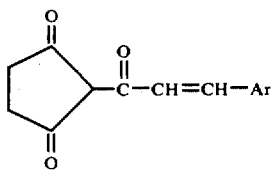

[IV]

where Ar is as defined above as the condensation product, and then reducing or hydrogenating this condensation product [IV] in a usual manner.

According to a particular embodiment of the second aspect of the present invention, there is further provided a process for the production of a derivative of 2-hydrocinnamoyl-1,3-cyclopentanedione of the formula:

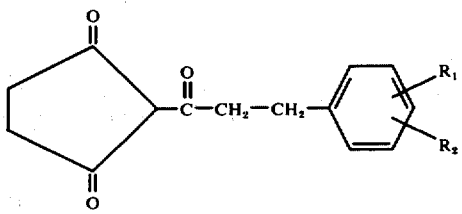

[Ia]

wherein $R_1$ and $R_2$ may be the same or different and are a hydrogen atom, a halogen atom, hydroxyl, nitro, cyano, trifluoromethyl, a lower alkyl of 1–4 carbon atoms, a lower alkoxyl of 1–4 carbon atoms, carbamoyl —$CONH_2$, a substituted amino group —NR'R'', an alkoxycarbonyl group -CO-OR' or an acyloxyl group -O-OCR' where R' and R'' may be the same or different and are a lower alkyl of 1–4 carbon atoms; or alternatively $R_1$ and $R_2$ together form a chain —O—R'''—O— where R''' is a lower alkylene of 1–4 carbon atoms, which comprises subjecting 2-acetyl-1,3-cyclopentanedione of the formula [II] and benzaldehyde of the formula:

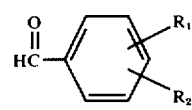

[IIa]

wherein $R_1$ and $R_2$ are as defined above to Claisen-Schmidt condensation in a usual manner to give a derivative of 2-cinnamoyl-1,3-cyclopentanedione of the formula:

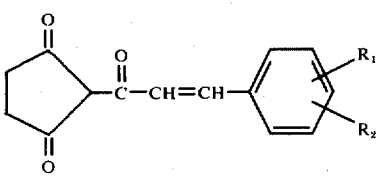

[IVa]

wherein $R_1$ and $R_2$ are as defined above, and then reducing or hydrogenating the resulting condensation product [IVa] in a usual manner.

In the process according to the second aspect of the present invention, the first step of condensing 2-acetyl-1,3-cyclopentanedione [II] with an aromatic aldehyde of the formula [III] or particularly benzaldehyde of the formula [IIIa] may be carried out in a usual manner which is known as Claisen-Schmidt condensation. It is preferred that a molar proportion of 2-acetyl-1,3-cyclopentanedione [II] is reacted with one to 10 molar proportions of the aromatic aldehyde [III] or [IIIa] in the presence of a condensation catalyst which may be a base. The reaction may take place in an organic solvent in which the reagents and the catalyst are soluble and which is inert to the condensation reaction. When the aromatic aldehyde reagent [III] or [IIIa] is in the form of a liquid, an excess of the aromatic aldehyde reagent may be used as the reaction medium or solvent. As the solvent which forms the reaction medium, there may be used any of methanol, ethanol, iso-propanol, tert-butanol, ethyl acetate, ethylene glycol, benzene, toluene, chloroform, methylene chloride, tetrahydrofuran, dioxan, dimethylsulfoxide (DMSO), dimethylformamide (DMF) and the like. For the base which serves as the condensation catalyst, there may be used any of bases which are known to promote the Claisen-Schmidt condensation process. The catalyst may suitably be an organic amine and preferably be a secondary amine such as morpholine, piperidine, and pyrrolidine etc. The base as the catalyst may usually be used in an amount of 0.1 to 10 mol. per mol. of the 2-acetyl-1,3-cyclopentanedione. The Claisen-Schmidt condensation step may preferably be carried out at a reaction temperature which is in a range of room temperature to about 100° C. In case the condensation reaction is effected at the temperatures of higher than 100° C, the yield of the condensation product [IV] or [IVa] can be deteriorated mainly due to the formation of tarry products. The first step of the process generally gives in a high yield a derivative of 2-cinnamoyl-1,3-cyclopentanedione [IV] or [IVa] which is usually a crystalline product of yellow to brown color.

With respect to the aromatic aldehyde [III] or [IIIa] which is used as one of the starting materials for the first step of the process, it may be un-substituted, mono-substituted or di-substituted on the aromatic nucleus. Thus, the aromatic aldehyde [III] or [IIIa] may be benzaldehyde itself, or may carry a substituent, for example, o-hydroxyl, m-hydroxyl, p-hydroxyl, o-methyl, p-methyl, o-methoxyl, m-methoxyl, p-methoxyl, o-chloro, m-chloro, p-chloro, o-fluoro, m-fluoro, p-fluoro, acetyloxy, p-methoxycarbonyl, p-carbamoyl, o-nitro, p-cyano, m-trifluoromethyl, p-(dimethyl)amino, etc., for either one of the substituents $R_1$ and $R_2$ on the aromatic ring of the formula [III] or on the phenyl ring of the formula [IIIa]. The benzaldehyde of the formula [IIIa] may also be di-substituted on the phenyl ring, for example, by pairs of o-hydroxyl and m-methoxyl; m-chloro and p-chloro; m-hydroxyl and p-hydroxyl; m-hydroxyl and p-methoxyl; or a chain - m-O-CH$_2$-p-O- (namely, 3,4-methylenedioxy) for both the substituents $R_1$ and $R_2$ on the phenyl ring thereof.

Since the condensation product [IV] or [IVa] may be obtained in a form of a salt of β-trione and the base, it is desirable to treat the salt with an acid such as hydrochloric or sulfuric acid to afford the free form of the condensation product [IV] or [IVa]. The intermediate condensation product [IV] or [IVa] which has been formed in the first step of the process is then subjected to a hydrogenation or reduction treatment in the second step of the process, so that it may be converted into the corresponding dihydro derivative, namely the corresponding derivative of 2-hydrocinnamoyl-1,3-cyclopentanedione [I] or [Ia] as the final product. The hydrogenation or reduction treatment which takes place in the second step of the process according to the second aspect of the present invention may be any of known methods of reduction or hydrogenation which are suitable to convert the olefinic double bond present in the derivative of 2-cinnamoyl-1,3-cyclopentanedione [IV] or [IVa] into the saturated single bond, as long as simultaneous hydrogenation of the β-trione group and the aromatic ring and particularly phenyl ring in the derivative of 2-cinnamoyl-1,3-cyclopentanedione [IV] or [IVa] can be avoided. As it is well known that the sensitivity of an aromatic ring, particularly phenyl ring to hydrogenation is different from the sensitivity of the olefinic double bond to hydrogenation, it is easy for the skilled in the art to select a procedure and reaction conditions for the hydrogenation by which the olefinic double bond may preferentially or selectively hydrogenated into the saturated alkylene bond without affecting or hydrogenating the aromatic ring, particularly phenyl ring which is present in the derivative of 2-cinnamoyl-1,3-cyclopentanedione [IV] or [IVa].

To reduce or hydrogenate the intermediate condensation product [IV] or [IVa] selectively into the final product [I] or [Ia] in the second step of the process according to the second aspect of the present invention, we prefer that the intermediate condensation product [IV] or [IVa] is subjected to a catalytic hydrogenation which may be carried out normally at room temperature and atmospheric pressure in the presence of a usual hydrogenation catalyst such as platinum, palladium, rhodium and Raney nickel etc. Platinum, palladium and rhodium may be supported by a suitable carrier such as carbon, if desired. This catalytic hydrogenation may preferably be effected in a solution of the intermediate condensation product [IV] or [IVa] in an organic solvent such as ethanol, tetrahydrofuran, dioxan and acetic acid etc. The hydrogenation catalyst may generally be used in an amount of 0.01% to 10% by weight of the intermediate condensation product. The catalytic hydrogenation may be continued until one mol. equivalent of hydrogen is absorbed by the reaction mixture. When the hydrogenation has been completed, the reaction mixture is freed from the catalyst, for example, by filtration and then distilled to remove the solvent. In this way, the derivative of 2-hydrocinnamoyl-1,3-cyclopentanedione [I] or [Ia] may be obtained substantially in a quantitative yield, and then it may be purified by recrystallisation, silica gel chromatography, alumina chromatography or any other suitable purification method to give the final product in a pure state and in an excellent yield.

The second process which is suitable for the production of the new derivative of 1,3-cyclopentanedione [I] comprises a single step of condensing 2-acetyl-1,3-cyclopentanedione [II] with an aromatic halide of the formula:

Ar—CH$_2$X         [V]

in which Ar is a mono-valent aromatic radical, substituted or un-substituted, as defined above and X is a halogen atom, for example, chlorine, bromine, iodine. This condensation reaction may be shown by the following equation:

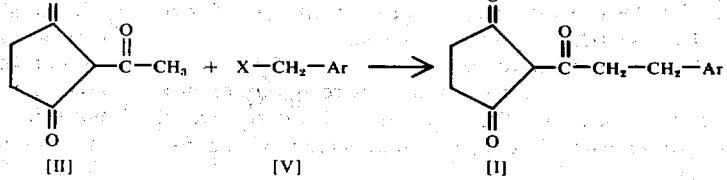

According to the third aspect of the present invention, therefore, there is a provided a process for the production of a derivative of 1,3-cyclopentanedione of the general formula:

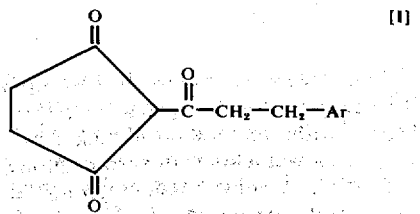

wherein Ar stands for a mono-valent aromatic radical, substituted or unsubstituted, which comprises condensing 2-acetyl-1,3-cyclopentanedione of the formula:

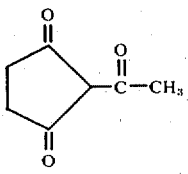

with an aromatic halide of the formula:

Ar—CH$_2$X  [V]

wherein Ar is as defined above and X is a halogen atom, in a known manner.

According to a particular embodiment of the third aspect of the present invention, there is provided a process for the production of a derivative of 2-hydrocinnamoyl-1,3-cyclopentanedione of the formula:

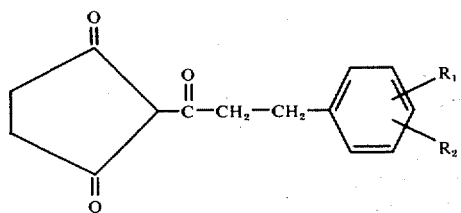

wherein R$_1$ and R$_2$ may be the same or different and each are a hydrogen atom, a halogen atom, hydroxyl, nitro, cyano, trifluoromethyl, a lower alkyl of 1–4 carbon atoms, a lower alkoxyl of 1–4 carbon atoms, carbamoyl group —CONH$_2$, a substituted amino group —NR'R'', an alkoxycarbonyl —CO-OR' or an acyloxyl group —O-OCR' where R' and R'' may be the same or different and are a lower alkyl of 1–4 carbon atoms; or R$_1$ and R$_2$ together form an alkylenedioxy chain -O-R'''-O- where R''' is a lower alkylene of 1–4 carbon atoms, which comprises condensing 2-acetyl-1,3-cyclopentanedione of the formula:

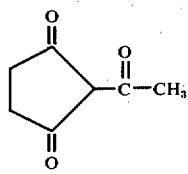

with a benzyl halide of the formula:

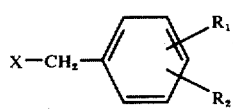

wherein R$_1$ and R$_2$ are as defined above and X is a halogen atom, in a known manner.

In the process according to the third aspect of the present invention, the condensation of 2-acetyl-1,3-cyclopentanedione [II] with an aromatic halide [V] or a benzyl halide [Va] may be carried out in such a manner and under such reaction conditions which are known as the dianion method of β-dicarbonyl compound, that is, the synthesis of γ-alkylation or γ-arylation through the dianion of β-diketone. We prefer that 2-acetyl-1,3-cyclopentanedione [II] is at first reacted with an alkali metal amide to give an alkali metal salt (namely, the dianion salt) of 2-acetyl-1,3-cyclopentanedione which is subsequently reacted with an aromatic halide [V] or a benzyl halide [Va]. This procedure may preferably be conducted in such a way that an alkali metal is dissolved in liquid ammonia suitably in the presence of a catalytic amount of ferric ion such as ferric nitrate, which promotes the formation of the alkali metal amide, the resulting solution of an alkali metal amide formed in liquid ammonia is reacted with 2-acetyl-1,3-cyclopentanedione, the formation of the alkali metal salt, namely the dianion salt of 2-acetyl-1,3-cyclopentanedione is effected in the liquid ammonia medium and then an aromatic halide [V] or a benzyl halide [Va] is reacted therewith in the same liquid ammonia medium. In this procedure, it is preferred to use liquid ammonia as the reaction medium, because this facilitates the formation of the alkali metal amide and the operation of this procedure. However, a suitable organic solvent, for example, tetrahydrofuran may be used as the reaction medium, if required. Sodium amide, lithium amide, potassium amide etc., may equally be used as the alkali metal amide for the purpose of forming an alkali metal salt (namely, the dianion salt) of 2-acetyl-1,3-cyclopentanedione, although sodium amide is most preferred among them.

In general, the condensation of 2-acetyl-1,3-cyclopentanedione [II] with an aromatic halide [V] or a benzyl halide [Va] may preferably be effected at a lower reaction temperature. Particularly in the above procedure where liquid ammonia is used as the reaction medium, it is necessary to effect the reaction normally at an extremely low temperature of −100° to −30° C in order to maintain the ammonia in the liquid state. When the desired condensation has been completed, the reaction mixture is raised to room temperature to distill off the excess of ammonia. The residue is treated with an acid such as hydrochloric acid and sulfuric acid so that the alkali metal salt, namely the monoanion form of the condensation product [I] or [Ia] which has been formed through the reaction of the alkali metal salt of 2-acetyl-1,3-cyclopentanedione with an aromatic halide [V] or a benzyl halide [Va] in the above-mentioned procedure is converted into the free form. The residue so treated is then extracted with a suitable organic solvent such as chloroform to recover the free form of the final product of the formula [I] or [Ia] which may, if desired, be further purified in a usual manner, for example, by chromatography. According to the abovementioned preferred procedure, the new derivative of 2-hydrocinnamoyl-1,3-cyclopentanedione [I] or [Ia] of the present invention may be obtained in a high yield and in a form of a high purity.

In the process according to the third aspect of the present invention, an aromatic halide [V] or a benzyl halide [Va] which is used as one of the starting materials therefor may be un-substituted, mono-substituted or di-substituted on the aromatic ring or the phenyl ring similarly to the aromatic aldehyde [III] or [IIIa] which is used as one reagent in the process of the second aspect of the present invention as stated above. The aromatic halide or benzyl halide used may suitably be the chloride, bromide or iodide.

The new compounds of the general formula [I] and particularly of the formula [Ia] according to the first aspect of the present invention are useful as a hypotensive agent, because they exhibit low toxicity and biological properties of strongly inhibiting the action of tyrosine hydroxylase and inhibiting the biosynthesis of norepinephrine as stated in the beginning of this specification.

Pharmacological properties of the new compounds of the present invention are now described. The new compounds of the present invention have been examined for their biological activities, and their inhibition to tyrosine hydroxylase are summarised in Table 2 later. The details of the test methods used and the close relationship of the biological activities between in vitro and in vivo are well presented in some published literatures (for example, see "J. Antibiot." 23, 514 (1970) and "J. Am. Chem. Soc." 93, 1285 (1971)). For instance, 2-(2-hydroxyhydrocinnamoyl)-1,3-cyclopentanedione, typical one of the new compounds of the present invention, was tested by dissolving in distilled water (pH was adjusted to 2.5) and administering to mice. It was then found that the $LD_{50}$ was 550 mg/Kg. in the oral administration and 283 mg/Kg. in the intraperitoneal injection. When 160 mg/Kg., 40 mg/Kg., and 10 mg/Kg. of 2-(2-hydroxyhydrocinnamoyl)-1,3-cyclopentanedione were orally or intraperitoneally given daily to mice for 30 days, none of toxic signs appeared except a decrease in the blood pressure. Effect of this compound on tyrosine hydroxylase was also tested by the method described in the "Journal of Antibiotics" 23, 514 (1970). In this test, the following inhibition % was observed at the following concentrations of 2-(2-hydroxyhydrocinnamoyl)-1,3-cyclopentanedione: 52% at 100 mcg/cc, 44% at 50 mcg/cc, 38% at 25 mcg/cc and 30% at 12.5 mcg/cc. When the test results were plotted according to Lineweaver-Burk equation, this compound showed uncompetitive relation with tyrosine and competitive relation with 2-amino-4-hydroxy-6,7-dimethyltetrahydropteridine.

Hydroxylation of tyrosine is the rate-limiting step of norepinephrine biosynthesis. Therefore, inhibition of tyrosine hydroxylase results in inhibition of norepinephrine synthesis in vivo which results in lowering the blood pressure. If norepinephrine synthesis in brain cells is reduced, it exhibits a sedative effect. The injection of a large dose of 2-(2-hydroxyhydrocinnamoyl)-1,3-cyclopentanedione to mice and rats did not cause sleeping and the sedative effect was not recognized. Therefore, it is suggested that blood brain barrier inhibits penetration of this compound into brain cells. Daily injection or daily oral administration of this compound to rats lowered the blood pressure. The hypotensive effect can be seen more markedly, when it is given to genetically hypertensive rats which was developed by Prof. Okamoto, Midical School, University of Kyoto. When 6.25 mg/Kg. was intraperitoneally injected to a rat of 185 mm. blood pressure and another rat of 188 mm., then the blood pressure was lowered to 25–155 mm. and 118–162 mm. respectively during 1–22 hours after the injection. When 125 mg/Kg. was intraperitoneally injected to a rat of 195 mm., the pressure was reduced to 155–166 mm. during 1–22 hours after the injection. The oral administration of this compound daily (3.1 mg/Kg., 6.25 mg/Kg., 12.5 mg/Kg., 25 mg/Kg.) for three days showed marked reduction of blood pressure. It caused 20–30% reduction which continued for about 5 days after the last oral administration.

2-(2-Hydroxyhydrocinnamoyl)-1,3-cyclopentanedione inhibits tyrosine hydroxylase and reduces blood pressure. Therefore, the combination with other hypotensive agents causes stronger effect.

The daily administration of 300 mcg (divided into three times) of 2-(2-hydroxyhydrocinnamoyl)-1,3-cyclopentanedione to hypertensive patients for 30 days showed hypotensive effect without any side effect.

According to a further aspect of the present invention, therefore, there is provided a new hypotensive agent comprising a derivative of 1,3-cyclopentanedione of the general formula [I] as defined above or a derivative of 2-hydrocinnamoyl-1,3-cyclopentanedione of the formula [Ia] as defined above, as the active ingredient thereof. The new compound of the formula [I] or [Ia] according to the present invention may be administered in various ways, for example, orally, intravenously, and intrarectally. Thus, it may be formulated in various forms such as powder, tablet, pill, capsule, pellete, syrup, injectable solution, suspension, suppository and such a pulverised sterile formulation which may be dissolved in sterile water to give an injectable solution immediately before use. In the solid formulations, any known pharmaceutially acceptable carrier such as lactose, starch and a known lubricating agent such as magnesium sterate may be mixed with the active compound of the present invention, as long as they are compatible with each other. For the therapeutic treatment of the hyperpiesia of adult man, effective dosage of the new compound of the present invention depends on the way of administration, but it has been found appropriate to administer a dose of 30 mg/Kg. to 1000 mg/Kg. per day to the hypertensive adult.

The invention is now illustrated by the following Examples 1–71 to which the present invention is limited in no way.

Examples 1 to 66 are illustrative of the process of the second aspect of the present invention where 2-acetyl-1,3-cyclopentanedione [II] is condensed with an aromatic aldehyde [III] or a benzaldehyde [IIIa] according to the Claisen-Schmidt condensation and the resulting intermediate condensation product [IV] or [IVa] is then hydrogenated. Among Examples 1 to 66, Examples 1 to 60 relate to the production of un-substituted and mono-substituted 2-hydrocinnamoyl-1,3-cyclopentanedione. Examples 67 to 71 are illustrative of the process of the third aspect of the present invention where 2-acetyl-1,3-cyclopentanedione [II] is condensed with an aromatic halide [V] or a benzyl halide [Va] by the dianion method.

EXAMPLE 1

This example explains the production of 2-hydrocinnamoyl-1,3-cyclopentanedione in two steps.

1. The preparation of 2-cinnamoyl-1,3-cyclopentanedione was conducted in the following way. A solution of 2.19 g. of 2-acetyl-1,3-cyclopentanedione, 3.56 g. of benzaldehyde and 0.5 ml. of morpholine in 100 ml. of benzene was refluxed for two hours while removal of water as formed was conducted by means of a water-collector. After the reaction, the benzene was removed under a reduced pressure, and the residue was dissolved in 100 ml. of methylene chloride. The solution was washed with 1N hydrochloric acid and then with brine, and it was dried over anhydrous sodium sulfate. After the removal of the solvent, the residue was subjected to silica gel chromatography, affording 1.48 g. (42%) of 2-cinnamoyl-1,3-cyclopentanedione as yellow crystals. This crystalline product was recrystallized from benzene-petroleum benzin, and the melting point should 114°–115° C.

| Elementary analysis | C(%) | H(%) |
|---|---|---|
| Found: | 73.74 | 5.18 |
| Calculated for $C_{14}H_{12}O_3$: | 73.67 | 5.30 |

2. The preparation of 2-cinnamoyl-1,3-cyclopentanedione was carried out in another way: Thus, a solution of 3.58 g. of 2-acetyl-1,3-cyclopentanedione, 5.13 g. of benzaldehyde and 2 cc. of morpholine in 120 ml. of ethanol was refluxed for 4.5 hours. After the reaction, the ethanol was distilled off under a reduced pressure. The residue was dissolved in 100 cc. of methylene chloride and the solution was washed with 1N hydrochloric acid and then brine, and it was then dried over sodium sulfate. A yellow colored crystalline product was obtained after removal of the solvent. This product was washed with cold benzene and petroleum benzin and dried to yield 4.82 g. (83%) of 2-cinnamoyl-1,3-cyclopentanedione.

3. Hydrogenation of 2-cinnamoyl-1,3-cyclopentanedione as prepared in the above step of Claisen-Schmidt condensation was carried out in the following way. 2-Cinnamoyl-1,3-cyclopentanedione (1.06 g.) was dissolved in 70 ml. of tetrahydrofuran, and the hydrogenation was effected in the presence of 0.15 g. of 5% palladium-on-charcoal at room temperature and under the atmospheric pressure. One mole of hydrogen was absorbed by the solution in 4 hours, and the tetrahydrofuran was distilled off under a reduced pressure to give a colorless crystalline product. Recrystallization from benzene-petroleum benzin gave 0.87 g. (81%) of 2-(hydrocinnamoyl)-1,3-cyclopentanedione of a melting point of 96°–97° C.

| Elementary analysis | C(%) | H(%) |
|---|---|---|
| Found: | 72.91 | 6.01 |
| Calculated for $C_{14}H_{14}O_3$: | 73.02 | 6.13 |

EXAMPLE 2

This example illustrates the production of 2-(3-hydroxyhydrocinnamoyl)-1,3-cyclopentanedione in two steps.

1. The preparation of 2-(3-hydroxycinnamoyl)-1,3-cyclopentanedione was conducted as follows: A solution of 2.43 g. of m-hydroxybenzaldehyde, 1.40 g. of 2-acetyl-1,3-cyclopentanedione and 1 ml. of morpholine in 50 ml. of ethanol was refluxed for 4.5 hours. After the reaction, the solvent was distilled off under a reduced pressure, and the residue was treated with 20 ml. of 1N hydrochloric acid to deposit a crystalline product which was then filtered off under a reduced pressure and washed with water and ethyl ether, yielding 2.56 g. of a yellow colored crystalline product. Recrystallization from methanolbenzene gave a product of a melting point of 217°–219° C which was identified as 2-(3-hydroxycinnamoyl)-1,3cyclopentanedione.

2. The hydrogenation of 2-(3-hydroxycinnamoyl)-1,3-cyclopentanedione as prepared in the preceding step was carried out by dissolving in ethanol in the presence of 5% palladium on charcoal at room temperature and under atmospheric pressure. 2-(3-Hydroxyhydrocinnamoyl)-1,3-cyclopentanedione was obtained in a quantitative yield, m.p 162°–165° C.

EXAMPLES 3–34

In these Examples, various derivatives of 2-cinnamoyl-1,3-cyclopentanedione of the formula [IVa] were prepared by condensing 2-acetyl-1,3-cyclopentanedione [II] with various benzaldehydes of the formula [IIIa] which have been un-substituted or mono-substituted on the phenyl ring, in the same manner as in the Claisen-Schmidt condensation step of Example 1 (1). Amount of 2-acetyl-1,3-cyclopentanedione of the formula [II], amount of the benzaldehyde of the formula [IIIa] used, natures of the substituents $R_1$ and $R_2$ in the benzaldehyde [IIIa] used, amount and nature of the secondary amines used as the condensation catalyst, amount and nature of the solvent used, and reaction time are tabulated in Table 1 below, and the yields of the derivative of 2-cinnamoyl-1,3-cyclopentanedione [IVa] obtained are also shown in Table 1 together with their melting points and elementary analysis data.

TABLE I

| Ex. | Amount (go) of the starting material (II) | Amount (go) of the benzaldehyde(IIIa) and nature of $R_1,R_2$ | Secondary amine, amount and nature thereof | Solvent, amount and nature thereof | Reaction time (hrs.) | Yield (%) of the product (IVa) | $R_1,R_2$ of the product (IVa) | M.P. (° C) of the product (IVa) | Elementary analysis (%) |
|---|---|---|---|---|---|---|---|---|---|
| 3 | 2.19g. | 3.56g. $R_1=R_2=H$ | Pyrrolidine, 0.05c.c. | Benzene, 100 c.c | 2 | 80 | $R_1=R_2=H$ | 114 – 115 | Found: C 73.74, H 5.18 Calcd.for $C_{14}H_{12}O_3$: C 73.67, H 5.30 |
| 4 | 2.20g. | 3.60g. $R_1=R_2=H$ | Piperidine 1 c.c. | Benzene, 100 c.c. | 2 | 82 | $R_1=R_2=H$ | 114 – 115 | |
| 5 | 10 g. | 12.4 g. $R_1=H$ $R_2=o$-OH | Morpholine, 5 c.c. | Methanol, 110 c.c. | 4 | 62 | $R_1=H$, $R_2=o$-OH | 188 – 189 | Found: C 68.41, H 4.88 Calcd.for $C_{14}H_{12}O_4$: C 68.84, H 4.95 |
| 6 | 1.93g. | 1.43g. $R_1=H$ $R_2=m$-OH | morpholine, 1 c.c. | Ethanol, 50 c.c. | 5 | 90 | $R_1=H$, $R_2=m$-OH | 217 – 219 | Found: C 68.69, H 5.02 Calcd.for $C_{14}H_{12}O_4$: C 68.84, H 4.95 |
| 7 | 5.48g. | 5.35g. $R_1=H$ $R_2=p$-OH | Morpholine, 5 c.c. | Ethanol, 50 c.c. | 4 | 91 | $R_1=H$, $R_2=p$-OH | 250 (Dec.) | Found: C 68.62, H 5.13 Calcd.for $C_{14}H_{12}O_4$: C 68.84, H 4.95 |
| 8 | 3.14g. | 6.23g. $R_1=H$, $R_2=p$-$CH_3O$ | Morpholine, 2 c.c. | Ethanol, 120 c.c. | 4.5 | 58 | $R_1=H$, $R_2=p$-$CH_3O$ | 123 – 125 | Found: C 69.48, H 5.48 Calcd.for $C_{15}H_{14}O_4$: C 69.75, H 5.46 |

TABLE I-continued

| Ex. | Amount (go) of the starting material (II) | Amount (go) of the benzaldehyde(IIIa) and nature of $R_1,R_2$ | Secondary amine, amount and nature thereof | Solvent, amount and nature thereof | Reaction time (hrs.) | Yield (%) of the product (IVa) | $R_1,R_2$ of the product (IVa) | M.P. (° C) of the product (IVa) | Elementary analysis (%) |
|---|---|---|---|---|---|---|---|---|---|
| 9 | 2.84g. | 5.26g. $R_1$=H, $R_2$=p-Cl | Morpholine, 4 c.c. | Ethanol, 120 c.c. | 4 | 75 | $R_1$=H, $R_2$=p-Cl | 163 – 165 | Found: C 63.93, H 4.24, Cl 13.49 Calcd.for $C_{14}H_{11}O_3Cl$: C 64.01,H 4.22,Cl 13.50 |
| 10 | 2.14g. | 4.47g. $R_1$=H, $R_2$=o-Cl | Morpholine, 4 c.c. | Ethanol, 120 c.c. | 4 | 90 | $R_1$=H, $R_2$=o-Cl | 172 – 173 | Found: C 63.91,H 4.21,Cl 13.38 Calcd.for $C_{14}H_{11}O_3Cl$: C 64.01,H 4.22,Cl 13.50 |
| 11 | 3.08g. | $R_1$=H, $R_2$=o-NO$_2$ | line, 2 c.c. | Ethanol, 150 c.c. | 2 | 37 | $R_1$=H, $R_2$=o-NO$_2$ | 173 – 175 | Found: C 61.36,H 4.14,N 5.04 Calcd.for $C_{14}H_{11}O_5N$: C 61.54,H 4.06,N 5.13 |
| 12 | 3.24g. | 5.84g. $R_1$=H, $R_2$=p-(CH$_3$)$_2$N | Morpholine, 4 c.c. | Ethanol 120 c.c. | 4 | 41 | $R_1$=H, $R_2$=p-(CH$_3$)$_2$N | 219 – 221 | Found: C 70.58,H 6.35,N 5.06 Calcd.for $C_{16}H_{17}O_3N$: C 70.83,H 6.32,N 5.16 |
| 13 | 2.98g. | 3.46g. $R_1$=H, $R_2$=m-F | Morpholine, 2 c.c. | Ethanol, 100 c.c. | 3 | 56 | $R_1$=H, $R_2$=m-F | 130 – 131 | Found: C 68.30,H 4.63,F 7.78 Calcd.for $C_{14}H_{11}O_3F$: C 68.29,H 4.50,F 7.72 |
| 14 | 3.42g. | 2.50g. $R_1$=H, $R_2$=p-F | Morpholine, 4 c.c. | Ethanol, 120 c.c. | 4.5 | 41 | $R_1$=H, $R_2$=p-F | 143 – 144 | Found: C 68.21,H 4.69,F 7.80 Calcd.for $C_{14}H_{11}O_3F$: C 68.29,H 4.50,F 7.72 |
| 15 | 2.50g. | 1.80g. $R_1$=H, $R_2$=o-F | Morpholine, 2 c.c. | Ethanol, 100 c.c. | 4 | 73 | $R_1$=H, $R_2$=o-F | 141 – 142 | Found: C 68.37,H 4.66,F 7.70 Calcd.for $C_{14}H_{11}O_3F$: C 68.29,H 4.50,F 7.72 |
| 16 | 3.00g. | 3.81g. $R_1$=H, $R_2$=o-CH$_3$O | Morpholine, 4 c.c. | Ethanol, 100 c.c. | 5 | 76 | $R_1$=H, $R_2$=o-CH$_3$O | 151 – 153 | Found: C 69.70, H 5.43 Calcd.for $C_{15}H_{14}O_4$: C 69.75, H 5.46 |
| 17 | 3.09g. | 5.78g. $R_1$=H, $R_2$=p-Br | Morpholine, 4 c.c. | Ethanol, 140 c.c. | 4 | 61 | $R_1$=H, $R_2$=p-Br | 178 – 180 | Found: C 54.75,H 3.56,Br 26.20 Calcd.for $C_{14}H_{11}O_3Br$: C 54.74,H 3.61,Br 26.02 |
| 18 | 4.21g. | 5.76g. $R_1$=H, $R_2$=p-CH$_3$ | Morpholine, 2 c.c. | Ethanol, 140 c.c. | 3.5 | 60 | $R_1$=H, $R_2$=p-CH$_3$ | 110 – 112 | Found: C 74.56, H 5.86 Calcd. for $C_{15}H_{14}O_3$: C 74.36, H 5.83 |
| 19 | 5.30g. | 7.19g. $R_1$=H, $R_2$=p-CH$_3$O—OC— | Morpholine, 4 c.c. | Ethanol, 160 c.c. | 4 | 50 | $R_1$=H, $R_2$=p-CH$_3$O—OC | 178 – 180 | Found: C 66.93, H 4.94 Calcd.for $C_{16}H_{14}O_5$: C 67.12, H 4.93 |
| 20 | 15.0g. | 30.5g. $R_1$=H, $R_2$=o-OH | Morpholine, 10 c.c. | DMSO, 300 c.c. | 17 mins | 69 | $R_1$=H, $R_2$=o-OH | 194 – 196 | Found: C 68.92 H 4.95 Calcd.for $C_{14}H_{12}O_4$: C 68.84, H 4.95 |
| 21 | 3.57g. | 3.61g. $R_1$=H, $R_2$=m-OH | Morpholine, 5.5 c.c. | Ethanol 160 c.c. | 4.5 | 50 | $R_1$=H, $R_2$=m-OH | 131 – 133 | Found: C 69.57, H 5.46 Calcd.for $C_{14}H_{14}O_4$: C 69.75, H 5.46 |
| 22 | 4.06g. | 5.21g. $R_1$=H $R_2$=p-C$_2$H$_5$O | Morpholine 6 c.c. | Ethanol 100 c.c. | 4 | 53 | $R_1$=H, $R_2$=p-C$_2$H$_5$O | 118 – 120 | Found: C 70.30, H 5.85 Calcd.for $C_{16}H_{16}O_4$: C 70.57, H 5.92 |
| 23 | 5.25g. | 6.97g. $R_1$=H, $R_2$=m-Br | Morpholine 7 c.c. | Ethanol 200 c.c. | 5 | 35 | $R_1$=H, $R_2$m-Br | 149 – 151 | Found: C 54.57,H 3.70,Br 26.25 Calcd.for $C_{14}H_{11}O_3Br$: C 54.74,H 3.61,Br 26.02 |
| 24 | 5.05g. | 6.70g. $R_1$=H, $R_2$=p-(CH$_3$)$_2$CH | Morpholine 7 c.c. | Ethanol, 160 c.c. | 5 | 73 | $R_1$=H, $R_2$=p-(CH$_3$)$_2$CH | 112 – 114 | Found: C 75.28, H 6.60 Calcd.for $C_{17}H_{18}O_3$: C 75.53, H 6.71 |
| 25 | 8.65g. | 9.46g. $R_1$=H, $R_2$=p-NO$_2$ | Morpholine 10 c.c. | DMSO, 100 c.c. | 23 mins (80° C) | 67 | $R_1$=H, $R_2$=p-NO$_2$ | 215 – 217 | Found: C 61.51,H 4.13,N 5.23 Calcd.for $C_{14}H_{11}O_5N$: C 61.54,H 4.06,N 5.13 |
| 26 | 5.17g. | 4.99g. $R_1$=H, $R_2$=p-CN | Morpholine 10 c.c. | DMSO, 100 c.c. | 35 mins (80° C) | 20 | $R_1$=H, $R_2$=p-CN | 177 – 179 | Found: C 71.13,H 4.50,N 5.41 Calcd.for $C_{15}H_{11}O_3N$: C 71.14,H 4.37,N 5.53 |
| 27 | 5.22g. | 5.66g. $R_1$=H, $R_2$=m-CF$_3$ | Morpholine 8 c.c. | Ethanol, 160 c.c. | 7 | 32 | $R_1$=H, $R_2$=m-CF$_3$ | 168 – 169 | Found: C 60.93,H 3.82,F 19.28 Calcd.for $C_{15}H_{11}O_3F_3$: C 60.81,H 3.74,F 19.24 |
| 28 | 50.0g. | 60.0g. $R_1$=H, $R_2$=p-CH$_3$O | Morpholine, 60 c.c. | t-Butanol, 1400 c.c. | 5 | 79 | $R_1$=H, $R_2$=p-CH$_3$O | 123 – 125 | |
| 29 | 5.03g. | 6.00g. $R_1$=H, $R_2$=p-CH$_3$O | Morpholine, 6 c.c. | Iso-propanol, 160 c.c. | 5 | 72 | $R_1$=H, $R_2$=p-CH$_3$O | 123 – 125 | |
| 30 | 4.92g. | 5.84g. $R_1$=H, $R_2$=p-CH$_3$O | Morpholine, 6 c.c. | n-Propanol, 160 c.c. | 4 | 42 | $R_1$=H, $R_2$=p-CH$_3$O | 123 – 125 | |
| 31 | 5.38g. | 6.48g. $R_1$=H, $R_2$=p-CH$_3$O | Morpholine, 6 c.c. | Ethyl acetate 160 c.c. | 5.5 | 49 | $R_1$=H, $R_2$=p-CH$_3$O | 123 – 125 | |
| 32 | 5.19g. | 6.99g. $R_1$=H, | Morpholine, 100 c.c. | DMF | 20 (room | 23 | $R_1$=H, $R_2$=o-OH | 188 – 189 | |

TABLE I-continued

| Ex. | Amount (go) of the starting material (II) | Amount (go) of the benzaldehyde(IIIa) and nature of $R_1,R_2$ | Secondary amine, amount and nature thereof | Solvent, amount and nature thereof | Reaction time (hrs.) | Yield (%) of the product (IVa) | $R_1,R_2$ of the product (IVa) | M.P. (° C) of the product (IVa) | Elementary analysis (%) |
|---|---|---|---|---|---|---|---|---|---|
| 33 | 10.0g. | $R_2$=o-OH 15.0g. $R_1$=H, $R_2$=o-OH | 5 c.c. Morpholine, 8 c.c. | DMSO, 200 c.c. | 21 (room temp.) | 63 | $R_1$=H $R_2$=o-OH | 188 – 189 | |
| 34 | 5.00g. | 6.00g. $R_1$=H $R_2$=o-CH$_3$CO—O— | Morpholine, 8 c.c. | Isopropanol, 160 c.c. | 20 (room temp.) | 52 | $R_1$=H, $R_2$=o-CH$_3$CO—O— | 160 – 161 | Found: C 66.96, H 4.91 Calcd.for C$_{16}$H$_{14}$O$_5$: C 67.12, H 4.93 |

EXAMPLES 35 – 60

In these Examples, various derivatives of 2cinnamoyl-1,3-cyclopentanedione of the formula [IVa] as prepared in Examples 3 – 34 were converted into the corresponding derivatives of 2-hydrocinnamoyl-1,3-cyclopentanedione of the formula [Ia] by hydrogenating them in the same manner as in the catalytic hydrogenation step of Example 1 (3). Nature of $R_1$ and $R_2$ in the resulting hydrogenation products 2-hydrocinnamoyl-1,3-cyclopentanediones [Ia], their yields, melting point and elementary analysis data are summarised in Table 2 with reference to the amount and nature of the catalyst and solvent which were employed in the catalytic hydrogenation step. In Table 2, there are also shown the degrees of inhibition (%) of the produced derivatives of 2-hydrocinnamoyl-1,3-cyclopentanedione [Ia] to tyrosine hydroxylase to provide a measure of their biological properties, the inhibition degrees as shown being determined by the same method as that used to estimate the inhibition % of 2-(2-hydroxyhydrocinnamoyl)-1,3-cyclopentanedione as mentioned above.

TABLE 2

| Example | Nature of $R_1,R_2$ in the hydrogenation product (Ia) | Catalyst | Solvent | Yield (%) of the product (Ia) | M.P. (° C) of the product (Ia) | Elementary analysis (%) | Inhibition of the product (Ia) to tyrosine hydroxylase (% meg.) |
|---|---|---|---|---|---|---|---|
| 35 | $R_1$=H, $R_2$=H | 5% Pd-C | Tetrahydrofuran | 85 | 96–97 | Found: C 72.91, H 6.01 Calcd. for C$_{14}$H$_{14}$O$_3$: C 73.02, H 6.13 | 60/100 |
| 36 | $R_1$=H, $R_2$=H | Pt | Ethanol | 90 | 96–97 | | |
| 37 | $R_1$=H, $R_2$=H | Ranney Ni | Ethanol | 80 | 96–97 | | |
| 38 | $R_1$=H, $R_2$=o-OH | 5% Pd-C | Ethanol | 57–79 | 119–120 | Found: C 68.41, H 5.65 Calcd. for C$_{14}$H$_{14}$O$_4$: C 68.28, H 5.73 | 52/100 |
| 39 | $R_1$=H, $R_2$=m-OH | 5% Pd-C | Tetrahydrofuran | 95 | 163–165 | Found: C 68.47, H 5.80 Calcd. for C$_{14}$H–O$_4$: C 68.28, H 5.75 | 23/100 |
| 40 | $R_1$=H $R_2$=p-OH | 5% Pd-C | Ethanol (equimolar amount of NaOH added) | 70 | 186–188 | Found: C 68.43, H 5.80 Calcd. for C$_{14}$H$_{14}$O$_4$: C 68.28, H 5.73 | 32/50 |
| 41 | $R_1$=H, $R_2$=p-CH$_3$O | 5% Pd-C | Tetrahydrofuran | 84 | 93–95 | Found: C 69.35, H 6.17 Calcd. for C$_{15}$H$_{16}$O$_4$: C 69.21, H 6.20 | 29/100 |
| 42 | $R_1$=H, $R_2$=o-Cl | 5% Pd-C | Dioxan | 78 | 102–103 | Found: C 63.82, H 4.98, Cl 13.07 Calcd. for C$_{14}$H$_{13}$O$_3$Cl: C 63.52, H 4.96, Cl 13.40 | 10/100 |
| 43 | $R_1$=H, $R_2$=p-Cl | 5% Pd-C | Tetrahydrofuran | 92 | 100–102 | Found: C 63.54, H 4.98, Cl 13.04 Calcd. for C$_{14}$H$_{13}$O$_3$Cl: C 63.52, H 4.96, Cl 13.40 | 42/100 |
| 44 | $R_1$=H, $R_2$=m-F | 5% Pd-C | Tetrahydrofuran | 90 | 73–74 | Found: C 67.81, H 5.37, F 7.72 Calcd. for C$_{14}$H$_{13}$O$_3$F: C 67.73, H 5.38, F 7.65 | 36/100 |
| 45 | $R_1$=H, $R_2$=p-F | 5% Pd-C | Tetrahydrofuran | 91 | 107–108 | Found: C 67.82, H 5.38, F 7.73 Calcd. for C$_{14}$H$_{13}$O$_3$F: C 67.73, H 5.28, F 7.65 | 62/200 |
| 46 | $R_1$=H, $R_2$=o-F | 5% Pd-C | Tetrahydrofuran | 95 | 86–87 | Found: C 67.85, H 5.34, F 7.69 Calcd. for C$_{14}$H$_{13}$O$_3$F: C 67.73, H 5.28, F 7.65 | 53/200 |

TABLE 2-continued

| Example | Nature of $R_1, R_2$ in the hydrogenation product (1a) | Catalyst | Solvent | Yield (%) of the product (1a) | M.P. (° C) of the product (1a) | Elementary analysis (%) | Inhibition of the product (1a) to tyrosine hydroxylase (% meg.) |
|---|---|---|---|---|---|---|---|
| 47 | $R_1$=H, $R_2$=o-$CH_3O$ | 5% Pd-C | Tetrahydrofuran | 94 | 95–97 | Found: C 69.18, H 6.23 Calcd. for $C_{15}H_{16}O_4$: C 69.21, H 6.20 | 7.6/200 |
| 48 | $R_1$=H, $R_2$=p-Br | 5% Pd-C | Tetrahydrofuran | 78 | 112–113 | Found: C 54.45, H 4.27, Br 25.90 Calcd. for $C_{14}H_{13}O_3Br$: C 54.39, H 4.24, Br 25.85 | 50/50 |
| 49 | $R_1$=H, $R_2$=p-$CH_3$ | 5% Pd-C | Tetrahydrofuran | 95 | 85–86 | Found: C 73.91, H 6.53 Calcd. for $C_{15}H_{16}O_3$: C 73.75, H 6.60 | 44/200 |
| 50 | $R_1$=H, $R_2$=p-$CH_3O$—OC | 5% Pd-C | Tetrahydrofuran | 92 | 116–117 | Found: C 66.51, H 5.52 Calcd. for $C_{16}H_{16}O_5$: C 66.66, H 5.59 | 41/200 |
| 51 | $R_1$=H, $R_2$=m-$CH_3O$ | 5% Pd-C | Tetrahydrofuran | 90 | 102–103 | Found: C 69.20, H 6.15 Calcd. for $C_{15}H_{16}O_4$: C 69.21, H 6.20 | 6.4/200 |
| 52 | $R_1$=H, $R_2$=p-$C_2H_5O$ | 5% Pd-C | Tetrahydrofuran | 92 | 85–88 Calcd. for $C_{16}H_{18}O$: | Found: C 70.12, H 6.60 C 70.05, H 6.61 | 15.6/200 |
| 53 | $R_1$=H, $R_2$=m-Br | 5% Pd-C | Tetrahydrofuran | 84 | 104–105 | Found: C 54.30, H 4.19, Br 25.60 Calcd. for $C_{14}H_{13}O_3Br$: C 54.39, H 4.24, Br 25.85 | 50.7/200 |
| 54 | $R_1$H, $R_2$=p-$CH(CH_3)_2$ | 5% Pd-C | Tetrahydrofuran | 89 | 83–84 | Found: C 75.15, H 7.38 Calcd. for $C_{17}H_{20}O_3$: C 74.97, H 7.40 | 36.8/200 |
| 55 | $R_1$=H, $R_2$=p-$C_2H_5O$—OC— | 5% Pd-C | Tetrahydrofuran | 85 | 85–86 | Found: C 67.81, H 6.06 Calcd. for $C_{17}H_{18}O_5$: C 67.54, H 6.00 | 12.8/200 |
| 56 | $R_1$=H, $R_2$=p-n-$C_3H_7O$—OC— | 5% Pd-C | Tetrahydrofuran | 90 | 51–53 | Found: C 68.41, H 6.17 Calcd. for $C_{18}H_{20}O_5$: C 68.34, H 6.37 | 4.6/200 |
| 57 | $R_1$=H, $R_2$=p-CN | 5% Pd-C | Tetrahydrofuran | 91 | 125–127 | Found: C 70.53, H 5.21, N 5.44 Calcd. for $C_{15}H_{13}O_3N$: C 70.58, H 5.13, N 5.49 | 77.4/200 |
| 58 | $R_1$=H, $R_2$=p-$(CH_3)_2N$—HCl | 5% Pd-C | Tetrahydrofuran | 80 | 151–152 | Found: C 62.08, H 6.55, N 4.44, Cl 11.47 Calcd. for $C_{16}H_{20}O_3NCl$: C 62.03, H 6.51, N 4.52, Cl 11.45 | 10.1/200 |
| 59 | $R_1$=H, $R_2$=m-$CF_3$ | 5% Pd-C | Tetrahydrofuran | 93 | 79–80 | Found: C 60.51, H 4.54, F 19.33 Calcd. for $C_{15}H_{13}O_3F$: C 60.40, H 4.39, F 19.11 | 30.5/200 |
| 60 | $R_1$=H, $R_2$=o-$CH_3CO$—O— | 5% Pd-C | Tetrahydrofuran | 80 | 85–87 | Found: C 66.87, H 5.53 Calcd. for $C_{16}H_{16}O_5$: C 66.66, H 5.59 | 10.0/100 |

EXAMPLE 61

2-Acetyl-1,3-cyclopentanedione (3.03 g.) was treated with 4-hydroxy-3-methoxybenzaldehyde (5.05 g.) in 50 ml. of dimethylsulfoxide at 80° C for 13 minutes in the presence of 4 ml. of morpholine. After cooling, 80 ml. of 1 N hydrochloric acid was added to the reaction mixture, depositing a crystalline product. The solid was collected by filtration, and washed with water and ethanol successively, and it was then dried. The Claiseu-Schmidt condensation product, 2-(4-hydroxy-3-methoxycinnamoyl)-1,3-cyclopentanedione, (1.3 g.) was obtained in an orange crystalline form, which showed mp. 274°–275° C after recrystallization from dioxane.

| Elementary analysis: | C (%) | H (%) |
|---|---|---|
| Found: | 65.85 | 5.06 |
| Calculated for $C_{15}H_{14}O_5$: | 65.69 | 5.15 |

The condensation product (577 mg.) was dissolved in ethanol and hydrogenated in the presence of 5% Pd-C at room temperature under atmospheric pressure. Fifty ml. of hydrogen (99% of the theoretical value) was absorbed in 6 hours 2-(4-Hydroxy-3-methoxyhydrocinnamoyl)-1,3-cyclopentanedione as yellow crystals was obtained in excellent yield (560 mg.), which showed mp. 209°–211° C after recrystallization from dioxane.

| Elementary analysis: | C (%) | H (%) |
|---|---|---|
| Found: | 65.21 | 5.84 |
| Calculated for $C_{15}H_{16}O_5$: | 65.20 | 5.64 |

This compound showed about 10% inhibition to tyrosine hydroxylase at a concentration of 200 mcg/cc.

EXAMPLE 62

2-Acetyl-1,3-cyclopentanedione (3.13 g.) was treated with 3,4-dichlorobenzaldehyde (4.36 g.) in 140 ml. of ethanol under reflux for 4 hours in the presence of 5 ml. of morpholine. After cooling, the reaction mixture was poured into 150 ml. of water containing 7 ml. of conc. hydrochloric acid. Deposited crystals were separated by filtration and washed with water, and dried. 2-(3,4-Dichlorocinnamoyl)-1,3-cyclopentanedione (2.48 g., 37%) was obtained which showed mp. 190°–191° C. after recrystallization from dioxane.

| Elementary analysis: | C (%) | H (%) | Cl (%) |
|---|---|---|---|
| Found: | 56.74 | 3.44 | 23.70 |
| Calculated for $C_{14}H_{10}O_3Cl_2$: | 56.59 | 3.39 | 23.87 |

The condensation product (0.63 g.) was dissolved in 50 ml. of dioxane and hydrogenated in the presence of 0.07 g. of 5% Pd-C at room temperature under atmospheric pressure. Fifty-two ml. of hydrogen was absorbed in 2 hours. After removal of the catalyst and solvent, 0.62 g. of 2-(3,4-dichlorohydrocinnamoyl)-1,3-cyclopentanedione was obtained, which showed mp. 126°–127° C. after recrystallization from a mixed solvent of ethanol and n-hexane.

| Elementary analysis: | C(%) | H(%) | Cl(%) |
|---|---|---|---|
| Found: | 56.29 | 4.10 | 23.55 |
| Calculated for $C_{14}H_{12}O_3Cl_2$: | 56.21 | 4.04 | 23.71 |

This compound showed 45% inhibition to tyrosine hydroxylase at a concentration of 100 mcg/cc.

EXAMPLE 63

2-Acetyl-1,3-cyclopentanedione (3.39 g.) was treated with piperonal (4.79 g.) in 60 ml. of dimethylsulfoxide in the presence of 5 ml. of morpholine at 85° C for 45 minutes. After cooling, the reaction mixture was poured into 150 ml. of water containing 7 ml. of conc. hydrochloric acid. Deposited crystals were separated by filtration and washed with water, and dried. 2-(3,4-Methylenedioxycinnamoyl)-1,3-cyclopentanedione (3.23 g.) was obtained in a yellow crystalline form, which showed mp. 181°– 182° C. after recrystallization from a mixed solvent of dioxane and ethanol.

| Elementary Analysis: | C (%) | H (%) |
|---|---|---|
| Found: | 66.25 | 4.42 |
| Calculated for $C_{15}H_{12}O_5$: | 66.17 | 4.44 |

The condensation product (1.95 g.) was dissolved in 150 ml. of tetrahydrofuran and hydrogenated in the presence of 0.20 g. of 5% Pd-C at room temperature under atmospheric pressure, absorbing 170 ml. of hydrogen in 5 hours. After removal of the catalyst and solvent, 1.89 g. of 2-(3,4-methylenedioxyhydrocinnamoyl)-1,3-cyclopentanedione was obtained, in the form of a light brown crystals which showed mp. 93°–94° C. after recrystallization from a mixed solvent of ethanol and n-hexane.

| Elementary analysis: | C (%) | H (%) |
|---|---|---|
| Found: | 65.61 | 5.22 |
| Calculated for $C_{15}H_{14}O_5$: | 65.69 | 5.15 |

This compound showed 22.5% inhibition to tyrosine hydroxylase at 100 mcg/cc.

EXAMPLE 64

2-Acetyl-1,3-cyclopentanedione (3.83 g.) was treated with 5.0 g. of 3-hydroxy-4-methoxybenzaldehyde in 120 ml. of ethanol in the presence of 5 ml. of morpholine under reflux for 5 hours. After cooling, the reaction mixture was poured into 200 ml. of water containing 8 ml. of conc. hydrochloric acid. Deposited crystals were separated by filtration, washed with water and ethanol successively, and dried. 2-(3-Hydroxy-4-methoxycinnamoyl)-1,3-cyclopentanedione (5.46 g.) was obtained, in the form of yellow crystals which showed mp. 137°–139° C. after recrystallisation from a mixed solvent of ethanol and dioxane.

| Elementary Analysis: | C (%) | H (%) |
|---|---|---|
| Found: | 66.99 | 5.87 |
| Calculated for $C_{16}H_{16}O_5$: | 66.66 | 5.59 |

The condensation product (3.79 g.) was dissolved in 200 ml. of tetrahydrofuran and hydrogenated in the presence of 0.30 g. of 5% Pd-C at room temperature under atmospheric pressure, absorbing 316 ml. of hydrogen in 3.5 hours. After removal of the catalyst and solvent, 3.80 g. of 2-(3-hydroxy-4-methoxyhydrocinnomoyl)-1,3-cyclopentanedione was obtained, in the form of yellow crystals which showed mp. 61°–62° C after recrystallization from a mixed solvent of ethanol and n-hexane.

| Elementary analysis: | C (%) | H (%) |
|---|---|---|
| Found: | 66.16 | 6.06 |
| Calculated for $C_{15}H_{18}O_5$: | 66.19 | 6.25 |

This compound showed 29.5% inhibition to tyrosine hydroxylase at 200 mcg/cc.

EXAMPLE 65

2-Acetyl-1,3-cyclopentanedione (4.26 g.) was treated with 4.94 g. of 2-hydroxy-3-methoxybenzaldehyde in 100 ml. of dimethylsulfoxide in the presence of 6 ml. of morpholine at 85° C for 40 minutes. After cooling, the reaction mixture was poured into 300 ml. of water containing 12 ml. of conc. hydrochloric acid. Deposited crystals were separated by filtration and washed with water, and dried. 2-(2-Hydroxy-3-methoxycinnamoyl)-1,3-cyclopentanedione (4.40 g., 49%) was obtained in yellow crystalline state, which showed mp. 198° – 200° C. after recrystallization from a mixed solvent of dioxane and ethanol.

| Elementary analysis: | C (%) | H (%) |
| --- | --- | --- |
| Found: | 65.58 | 5.26 |
| Calculated for $C_{15}H_{14}O_5$: | 65.69 | 5.15 |

The condensation product (1.65 g.) was dissolved in 200ml. of tetrahydrofuran (THF.) and hydrogenated in the presence of 0.20 g. of 5% Pd-C at room temperature under atmospheric pressure, absorbing 120 ml. of hydrogen in 2 hours. After removal of the catalyst and solvent, 1.55 g. of 2-(2-hydroxy-3-methoxyhydrocinnamoyl)-1,3-cyclopentanedione was obtained, in lightly yellow crystalline form which showed mp. 108° – 109° C. after recrystallization from a mixed solvent of benzene and n-hexane.

| Elementary analysis: | C (%) | H (%) |
| --- | --- | --- |
| Found: | 65.20 | 5.89 |
| Calculated for $C_{15}H_{16}O_5$: | 65.21 | 5.84 |

This compound showed 5% inhibition to tyrosine hydroxylase at 100 mcg/cc.

EXAMPLE 66

2-Acetyl-1,3-cyclopentanedione (3.98 g.) was treated with 3.57 g. of 3,4-dihydroxybenzaldehyde in 50 ml. of dimethylsulfoxide in the presence of 5 ml. of morpholine at 80° C. for one hour. The reaction mixture was poured into 200 g. of ice-water containing 10 ml. of conc. hydrochloric acid. Reddish crystals thus obtained were separated by filtration, washed with water and ethanol successively, and dried. 2-(3,4-Dihydroxycinnamoyl)-1,3-cyclopentanedione (3.98 g.) was recrystallized from methanol, showing mp. 275°–277° C.(Dec.)

| Elementary analysis: | C (%) | H (%) |
| --- | --- | --- |
| Found: | 64.34 | 4.68 |
| Calculated for $C_{14}H_{12}O_5$: | 64.61 | 4.65 |

The condensation product (0.82 g.) was dissolved in 10 ml. of water containing 9.45 ml. of 1N sodium hydroxide solution, and hydrogenated in the presence of 0.08 g. of 5% Pd-C at room temperature under atmospheric pressure, absorbing 77 ml. of hydrogen for 1.5 hours. After removal of the catalyst and neutralization with 6 ml. of 2N hydrochloric acid, there was obtained 0.60 g. (73%) of 2-(3,4-dihydroxyhydrocinnamoyl)-1,3-cyclopentanedione in a yellow crystalline form which showed mp. 210° – 211° C after recrystallization from methanol.

| Elementary analysis: | C (%) | H (%) |
| --- | --- | --- |
| Found: | 64.21 | 5.27 |
| Calculated for $C_{14}H_{14}O_5$: | 64.11 | 5.38 |

This compound showed a strong inhibition (85%) to tyrosine hydroxylase at 100 mcg/cc.

EXAMPLE 67

Fresh sodium amide was prepared by adding 1.2 g. methallic sodium to 250 ml. of liquid ammonia in the presence of a catalytic amount (19 mg.) of ferric sulfate at −70° C. in a 500 ml. three-necked flask equipped with a calcium chloride tube, a dry-ice reflux condenser with a thermometer, and an inlet-tube of nitrogen. 2-Acetyl-1,3-cyclopentanedione (3.25 g.) dissolved in 10 ml. of anhydrous tetrahydrofuran was added to the liquid ammonia solution with stirring and the vessel was kept at the boiling temperature of ammonia for 2 hours. A solution of 4.23 g. of p-chlorobenzylchloride dissolved in 5 ml. of anhydrous ethyl ether was added to the liquid ammonia solution over 20 minutes under stirring at −30° C. under passing nitrogen therethrough. After three hours reflux of the reaction mixture at −30° C, it was allowed to stand overnight at room temperature to remove ammonia. The residue was extracted with chloroform after acidification with 2N hydrochloric acid. The organic layer was dried over anhydrous sodium sulfate and the solvent was distilled off to leave 5.68 g. of an orange solid. It was subjected to silica gel chromatography, affording 2.79 g. of a pale yellow crystalline product 2-(4-chlorohydrocinnamoyl)-1,3-cyclopentanedione. This compound was found to be identical with an authentic sample which was prepared from 2-acetyl-1,3-cyclopentanedione and 4-chlorobenzaldehyde by the Claisen-Schmidt condensation followed by the hydrogenation in Example 43.

EXAMPLE 68

Fresh sodium amide was prepared by adding 1.2 g. of metallic sodium to 200 ml. of liquid ammonia in the presence of a catalytic amount (106 mg.) of ferric sulfate at −70° C in a 500 ml. three-necked flask equipped with a calcium chloride tube, a dry-ice reflux condenser with a thermometer, and an inlet-tube of nitrogen. 2-Acetyl-1,3-cyclopentanedione (3.5 g.) dissolved in 10 ml. of tetrahydrofuran was added to the sodium amide solution in liquid ammonia and treated at the boiling temperature of ammonia for 1 hour. Benzylchloride (3.2 g.) dissolved in 5 ml. of absolute ethyl ether was added to the liquid ammonia solution over 20 minutes, and the reaction mixture was allowed to stand over night at the boiling temperature of ammonia and at room temperature to remove the ammonia. The residue was extracted with ether after acidification with 2N hydrochloric acid. The ethereal solution was dried over sodium sulfate and the solvent was removed. The residue was subjected to silica gel chromatography using chloroform as the eluting solvent, to give 1.74 g. (30.2%) of 2-hydrocinnamoyl-1,3-cyclopentanedione. This compound was found to be identical with an authentic sample which was prepared from 2-acetyl-1,3-cyclopentanedione and benzaldehyde in Example 35.

EXAMPLE 69

This example explains the preparation of 2-(2-chlorohydrocinnamoyl)-1,3-cyclopentanedione. Fresh sodium amide was prepared by adding 1.2 g. of sodium metal to about 300 ml. of ammonia in the presence of a catalytic amount (29 mg.) of ferric chloride as described in Example 67. 2-Acetyl-1,3-cyclopentanedione (3.2 g.) dissolved in absolute tetrahydrofuran was added to the above ammonia solution to give the dianion salt, which was then treated with 4.25 g. of o-chlorobenzylchloride in the same manner as described in Example 67. After removal of ammonia, extraction with ether and silica gel chromatography, 3.15 g. (52%) of 2-(2-chlorohydrocinnamoyl)-1,3-cyclopentanedione was obtained as pale yellow crystals.

EXAMPLE 70

This example explains the preparation of 2-hydrocinnamoyl-1,3-cyclopentanedione. Fresh sodium amide was prepared from 1.2 g. of sodium metal and 250 ml. of ammonia in the same manner as described in Example 67. 2-Acetyl-1,3-cyclopentanedione (3.22 g.) dissolved in absolute tetrahydrofuran was added to the sodium amide solution in liquid ammonia, and the dianion thus formed was treated with 4.45 g. of benzylbromide in a manner similar to Example 67, affording 3.88 g. (64%) of 2-hydrocinnamoyl-1,3-cyclopentanedione as pale yellow crystals.

EXAMPLE 71

This example explains the preparation of 2-(4-methylhydrocinnamoyl)-1,3-cyclopentanedione. Fresh sodium amide was prepared by adding 1.2 g. of sodium metal to about 300 ml. of ammonia in the presence of a catalytic amount (32 mg.) of ferric chloride as described in Example 67. 2-Acetyl-1,3-cyclopentanedione (3.2 g.) dissolved in 10 ml. of absolute tetrahydrofuran was added to the ammonia solution to give the dianion salt which was then treated with 3.64 g. of p-methylbenzaldehyde in a similar manner to Example 67. After removal of ammonia, extraction with ether and silica gel chromatography, 3.04 g. (48%) of 2-(4-methylhydrocinnamoyl)-1,3-cyclopentanedione was obtained as pale brown crystals.

What we claim is:

1. 2-hydrocinnamoyl-1,3-cyclopentanedione of the formula:

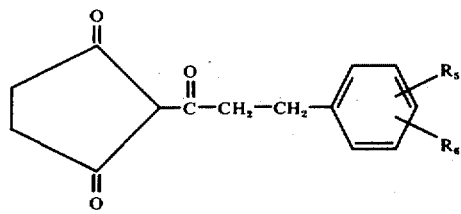

wherein $R_5$ and $R_6$ may be the same or different and may be halogen, hydroxyl, a lower alkyl of 1–4 carbon atoms or a lower alkoxyl of 1–4 carbon atom.

2. 2-hydrocinnamoyl-1,3-cyclopentanedione of the formula:

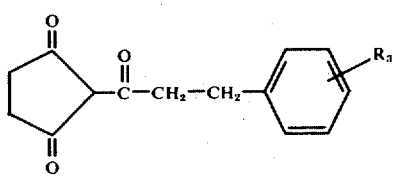

wherein $R_3$ is a hydrogen atom, a halogen atom, hydroxyl, nitro or a lower alkoxyl of 1–4 carbon atoms.

3. 2-hydrocinnamoyl-1,3-cyclopentanedione of the formula:

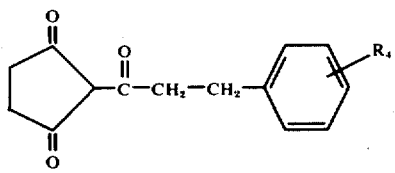

wherein $R_4$ is a hydrogen atom or a lower alkyl of 1–4 carbon atoms.

4. 2-(Hydrocinnamoyl)-1,3-cyclopentanedione.
5. 2-(2-Hydroxyhydrocinnamoyl)-1,3-cyclopentanedione.
6. 2-(3-Hydroxyhydrocinnamoyl)-1,3-cyclopentanedione.
7. 2-(4-Hydroxyhydrocinnamoyl)-1,3-cyclopentanedione.
8. 2-(3,4-Dihydroxyhydrocinnamoyl)-1,3cyclopentanedione.
9. 2-(4-Chlorohydrocinnamoyl)-1,3-cyclopentanedione.
10. 2-(4-Fluorohydrocinnamoyl)-1,3-cyclopentanedione.
11. 2-(4-Nitrohydrocinnamoyl)-1,3-cyclopentanedione.
12. 2-(4-Methylhydrocinnamoyl)-1,3-cyclopentanedione.
13. 2-(4-Methoxyhydrocinnamoyl)-1,3-cyclopentanedione.

* * * * *